United States Patent [19]

Tracy et al.

[11] Patent Number: 4,842,858

[45] Date of Patent: Jun. 27, 1989

[54] POLYMERIC HALOPHORS

[75] Inventors: David J. Tracy, Lincoln Park; Mohamed M. Hashem, Wayne; Robert B. Login, Oakland, all of N.J.

[73] Assignee: GAF Corporation, Wayne, N.J.

[21] Appl. No.: 131,789

[22] Filed: Dec. 11, 1987

Related U.S. Application Data

[62] Division of Ser. No. 21,284, Mar. 3, 1987.

[51] Int. Cl.$^4$ .................. A61K 31/395; C11D 1/58; C11D 3/58
[52] U.S. Cl. ........................... 424/150; 424/78; 252/106
[58] Field of Search ............... 252/106; 424/150, 78; 514/128, 210, 212, 277

[56] References Cited

U.S. PATENT DOCUMENTS 4,017,407  4/1977  Cantor et al. .................. 252/106
4,113,857  9/1978  Shetty ............................. 424/150

*Primary Examiner*—Allan M. Lieberman
*Attorney, Agent, or Firm*—Marilyn J. Maue; Joshua J. Ward

[57] ABSTRACT

A stable iodine complex formed from the association of iodine with a pyrrolidonyl surfactant and its use in therapeutic, environmental and industrial applications and particularly as low foaming disinfectants for gradual release of iodine over significantly extended periods.

12 Claims, No Drawings

POLYMERIC HALOPHORS

This is a division of application Ser. No. 021,284, filed Mar. 3, 1987.

Iodine complexes with methyl pyrrolidone for germicidal and disinfectant applications has long been known. However, the iodine disinfectant properties of this complex is dissipated in a relatively short period so that reapplication of the disinfectant treatment is required for protection over long periods. Also, for certain applications, e.g. washing of contaminated equipment, hospital surroundings and animal disinfection, cleaning as well as germicidal, virucidal and sporicidal properties are required. Iodine/polyvinyl pyrrolidone complexes, which present numerous complexing sites in the molecule, have been developed for this purpose and, while these polymeric complexes, do in fact, extend the effective release of iodine over longer periods, they, like the methyl pyrrolidone/iodine complexes, lack the desired surfactant and detergent properties. Therefore, it is an aim of research to develop a disinfectant or germicide having extended iodine release time as well as non-foaming surfactant and cleaning properties so that such treatment need not be frequently repeated and removal of other soil or debris can be accomplished in a single washing treatment.

Accordingly it is an object of this invention to accomplish the above sought for needs.

Another object of this invention is to provide the release of iodine over an extended period of time by a method which is commercially feasible and economical.

Another object is to provide a low foaming surfactant which inherently possesses disinfectant properties.

These and other objects of the invention will become apparent from the following description and disclosure.

The above and other objects and benefits are achieved by providing iodine or bromine complexes of a pyrrolidonyl alkyleneoxy polymer wherein the halogen is complexed with the pyrrolidone ring as well as the alkyleneoxy group in the polymer chain. More specifically, the compounds of this invention are the halogen complexes of pyrrolidonyl alkyleneoxy polymers which possess high skin substantivity and excellent disinfectant, bactericide, sporicidal, virucidal and surfactant and coating properties.

The complexing polymers of this invention are those containing an alkyleneoxy pyrrolidonyl unit of the type:

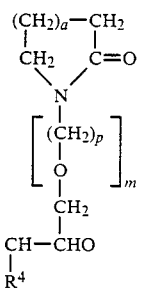

A.

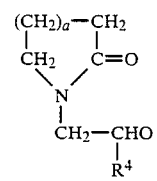

B.

wherein $R^4$ is H or $CH_3$; a has a value of 1–3; m has a value of 0 or 1 and p has a value of 1 or 2, said polymers also containing at least one or more hydrophobic groups. Generally, the polymeric complexing agents contain an ethyleneoxy group, referred to herein as EO, and/or a propyleneoxy group, referred to herein as PO in the polymer chain.

The halogen complexes of the present invention are iodophors or bromophors and, where complexing takes place, stable complexed sites are formed. The halogen present in the complexed copolymer as available iodine or bromine can range between about 2% and about 40%, preferably between about 5% and about 25%, depending on the amount of disinfectant properties desired in the product.

Representative species of the pyrrolidonyl alkyleneoxy block copolymers with which iodine or bromine can be complexed, include the following types C–F.

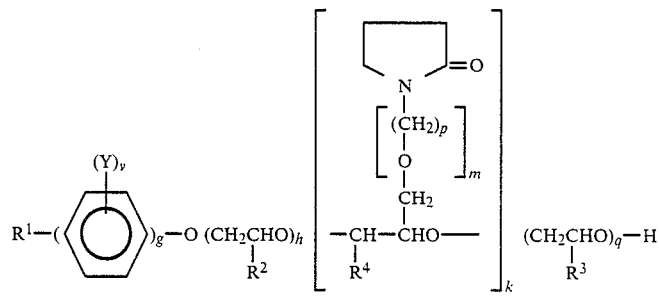

wherein at least one of $R^2$ and $R^3$, when present in the copolymer, is methyl; the remaining of groups $R^2$ and $R^3$, when present in the copolymer, being either hydrogen or methyl; $R^1$ is alkyl having from 6 to 20 carbon atoms; Y is alkyl having from 1 to 4 carbon atoms; v has a value of 0 to 2; each of h and q have a value of from 0 to 100 and at least one of h and q is a positive integer, preferably an integer greater than one.

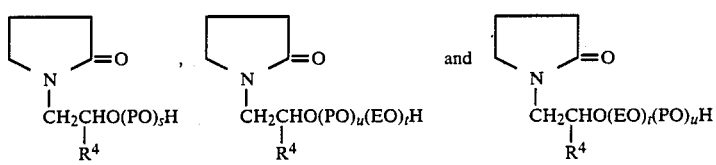

D.

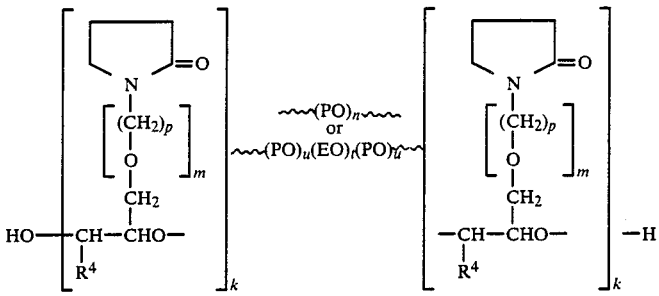

E.

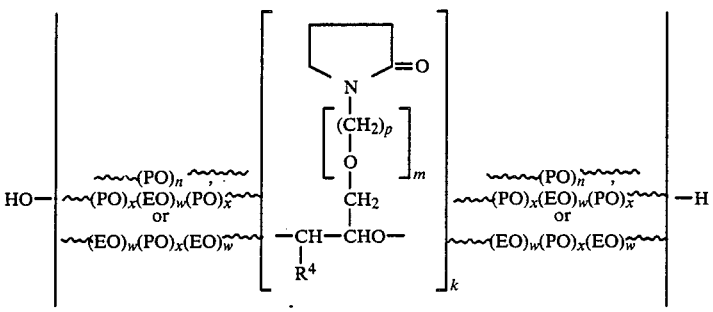

F.

wherein $R^4$, m and p are as defined above; and g, h, k, n, q, s, t, u, v, w and x are integers having the following values

| | |
|---|---|
| g = 0 or 1; | s = 2 to 200; |
| h = 0 to 100; | t = 2 to 50; |
| k = 2 to 200; | u = 2 to 50; |
| n = 1 to 100; | v = 0 to 2; |
| q = 0 to 100; | w = 1 to 25 and |
| | x = 1 to 25. |

Since these units may occur in block or random distribution in the polymeric product, it is to be understood that their subscripts in the formulae represent the total number of designated units in the polymer and not the order of unit succession; although these units may occur in block segments as indicated above.

Preparations for the above polymers C–E are known. Specifically, the polymers of Group C where q and m are zero, and h is a positive integer are prepared by reacting an alkyleneoxylated alkylphenol with an epoxyalkyl-2-pyrrolidone or, when m has a value of 1 and p has a value of 2, by reacting an alkyleneoxylated alkylphenol with the glycidol ether of N-hydroxyethyl pyrrolidone, at a temperature of between about 100° C. and about 150° C. for 0.5 to 5 hours under atmospheric pressure. When m is a positive integer the polymer is prepared by reacting an aliphatic or aromatic alcohol with glycidyl ether of N-hydroxyethylpyrrolidone under the above conditions. When q is a positive integer, either of the above products are further reacted with the corresponding alkylene oxide under the above conditions.

The polymers of Group D are prepared by reacting 2-pyrrolidone with an alkylene oxide, such as propylene oxide in the presence of an alkali metal hydroxide, e.g. sodium hydroxide at a temperature between about 110° C. and about 175° C. under 15 to 50 psig. for a period of from about 0.5 to about 10 hours. When PO and EO units in the polymer are desired, the above product of Group D is further reacted with the appropriate alkylene oxide at a temperature of between about 110° C. and about 175° C. under 15 to 50 psig. for a period of from about 0.5 to about 10 hours.

The polymers of Group E are prepared by reacting polypropylene glycol with epoxypropylpyrrolidone or the glycidyl ether of N-hydroxyethylpyrrolidone at a temperature of between about 100° C. and about 150° C. under from about 14 to about 50 psig. for a period of from about 0.5 to about 10 hours.

As in copending application Ser. No. 020,841, now U.S. Pat. No. 4,698,412, filed concurrently herewith, the polymers of Group F can be prepared by reacting a poly(N-pyrrolidonyl methyl)ethylene glycol with propylene oxide or a combination of propylene oxide and ethylene oxide under from about 14 to about 50 psig at between about 100° C. and about 150° C. for a period of from about 0.5 to about 15 hours.

Generally, any of the polymers disclosed in co-pending patent application Ser. No. 021,053, filed 03/02/87, now U.S. Pat. No. 4,801,400 entitled Epoxy Pyrrolidone Based Non-Ionic Surfactants, may be employed as a suitable polymeric moiety for complexing with iodine or bromine.

The preparation of the present complex is achieved by an economical and commercially feasible process. More particularly, iodine, bromine or a mixture of halogen and the corresponding hydrogen halide or inorganic halide salt such as the sodium or potassium salt of iodine or bromine is contacted with the pyrrolidonyl surfactant polymer. The mole ratio of halogen to hydrogen halide or inorganic halide salt employed in the present process is between about 2:1 and about 10:1, preferably between about 3:1 and about 8:1 and the concentration of halogen based on polymer is between about 10% and about 50% by weight, preferably between about 20% and about 30% by weight. The vapor pressure of the halogen during complexing is reduced essentially to zero providing a stable complexed product.

The complexing reaction is effected at a temperature between about 20° and 85° C., preferably between 40° and about 60° C. with constant agitation under atmospheric pressure. The addition of halogen plus halide solution to polymer is accomplished in a period of from 5 minutes to 2 hours, preferably from about 20 to 45 minutes.

The complexed products of this invention can be formulated as a concentrate with disinfecting washing formulations and concentrations of the present complexes between about 0.1 and about 15 weight % of active ingredients are effective in providing an increased non-foaming cleansing action coupled with germicidal and insecticidal disinfecting properties. The optimum weight concentration of the present complexes in the concentrate formulation falls within the range of from about 0.8 to about 5 weight %.

A typical disinfectant and cleaning concentrate is represented by the formulation:

| Components | wt. % |
|---|---|
| halophor complex, e.g. | 8.75 |
| $C_9H_{19}-C_6H_4-O-(CH_2-CH-O)_4-H$ with $CH_2-N$-pyrrolidonyl substituent | |
| phosphoric acid (75%) | 8.0 |
| iodophor base (nonionic) | 5.0 |
| water | 78.25 |

The above formulation has 1.75% available iodine Aliquats of 25 to 100 ppm iodine can then be made up as the disinfectant cleaning solution. The resulting solutions are lower foaming than conventional products, as demonstrated in the following examples, and are milder to the skin and stable at elevated temperatures over extended periods.

Reference is now made to the following examples which illustrate preferred embodiments but which are not to be construed as limiting to the scope of the invention as more broadly set forth above and in the appended claims.

EXAMPLE 1

Preparation of

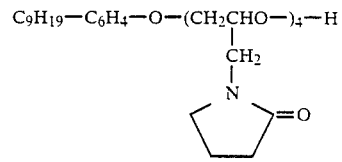

To 41.2 g. (0.2 mole) of nonylphenol in a round bottom flask was added 0.4 g. of potassium hydroxide. The mixture was heated to 120° C. under vacuum to remove water, after which 112.8 g. (0.8 mole) of N-epoxypropylpyrrolidone was added at a temperature of from 115° C. to 125° C. over a period of 1.5 hours. After addition, the resulting mixture was held at about 115° C. for an additional 3 hours. The mixture was then cooled and then neutralized with 0.4 g. of glacial acetic acid. The product had a cloud point of 70.5°–71° C. (1% in water).

The iodophor of the above Example was prepared by adding 49.7 g. of iodine over a period of 30 minutes to a solution of 140 g. of nonylphenol-4N-epoxypropyl-2-pyrrolidone adduct, in 13.3 g. of water containing 17.6 g. of sodium iodide at a temperature of 40°–45° C. After the addition, the reaction mixture was held for 2 hours at 40°–45° C. The resulting iodine complex was found to have 22.5% available iodine.

EXAMPLE 2

Preparation of

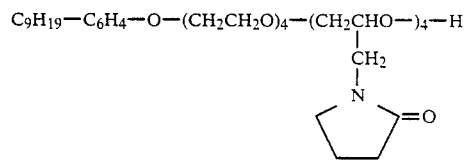

To 76.4 g. (0.2 mole) of nonylphenol-4 ethylene oxide adduct (IGEPAL CO 430) was added over a period of 2 hours at a temperature of 115°–120° C., 112.8 g. (0.8 mole) of 2,3-epoxypropyl-2-pyrrolidone. After the addition, the reaction mixture was held at 145° C. for 4 hours after which the product was cooled to room temperature. The product had a cloud point above 100° C. The iodophor of the above product was prepared by adding 49.7 g. of iodine over a period of 30 minutes to a solution containing 140 g. of the epoxypropylpyrrolidone polymer obtained above in 13.3 g. of water containing 17.6 g. of sodium iodide at a temperature of 40°–45° C. After the addition, the reaction mixture was held for 2 hours at 40°–45° C. to form the corresponding complexed compound.

EXAMPLE 3

Preparation of

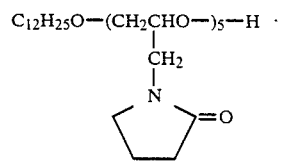

To 37.2 (0.2 mole) of dodecanol was added 0.4 g. potassium hydroxide and the mixture was sparged for 30 minutes at 110°–115° C. with nitrogen. To this mixture was added over a 2 hour period, 141.0 g. (1.0 mole) of 2,3-epoxypyrrolidone and the resulting reaction mixture was held for an additional 3 hours at 110°–120° C. The product was then cooled and then neutralized with glacial acetic acid and was found to have a cloud point of 67°–68° C. (1% in 10% NaCl).

The iodophor of the above compound is prepared according to the methods set forth in Example 1 employing 49.7 g. of iodine, 140 g. polymer, 13.3 g. water and 17.6 g. sodium iodide.

EXAMPLE 4

Preparation of

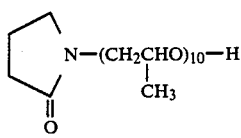

To a one liter autoclave was charged 85 g. (1.0 mole) of pyrrolidone and 0.5 g. of sodium hydroxide flakes. To this mixture was added 580 g. (10 moles) of propylene oxide over a period of 5 hours at a temperature of 160° C. under 15–30 psig. The resulting mixture was agitated for 30 minutes at 160° C., after which it is cooled to 65° C. and a house vacuum was applied to degas the mixture. The product (434 g.) was neutralized to a pH of 7.4 by addition of phosphoric acid. Product analysis by NMR indicated that 9.7 of the propylene oxide molecules had reacted.

EXAMPLE 5

Preparation of

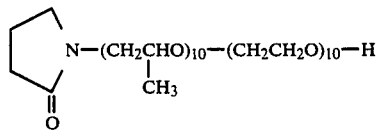

To a one liter autoclave was charged 266.0 g. (0.4 mole) of the pyrrolidone-10 propylene oxide adduct from Example 4 and 176.0 g. (4.0 moles) of ethylene oxide was added over a period of 5 hours at 140°–160° C. under a pressure of 15 to 30 psig. The mixture was held at this temperature for an additional 30 minutes, after which the product 434 g. was cooled, discharged and neutralized with 85% phosphoric acid. By NMR analysis, it was found that the product contained 8.4 moles of ethylene oxide. The product was found to have a cloud point of 67° C. (1% in water).

The iodophor of the above product was prepared by adding to 139.4 g. (0.126 mole) of the above pyrrolidone-PO-EO adduct at a temperature of 40°–45° C., 13.3 g. of water containing 17.6 g. of sodium iodide. To this solution was added over a period of 30 minutes, 49.7 g. (0.39 mole) of iodine and the resulting mixture was held for an additional 2 hours at 40°–45° C. The complexed product recovered was found to have 20.6% available iodine and 28.7% total iodine.

EXAMPLE 6

Preparation of

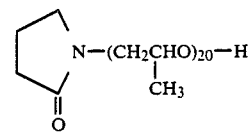

Example 4 was repeated except that 20 moles of propylene oxide is substituted therein. NMR analysis showed that 20 moles of propylene oxide had reacted. The material was found to be insoluble in water.

EXAMPLE 7

Preparation of

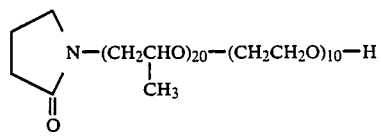

Using 0.4 mole of the product of Example 6, the procedure set forth in Example 5, reacting 4.0 moles of ethylene oxide is repeated. The resulting product has a cloud point of 38° C. (1% in water).

The iodophor of the product of this Example is prepared by adding 12 g. of water containing 13.4 g. of sodium iodide at 40° C. to 105.2 g. (0.06 mole) of the product of this Example. After the solution is clear, 37.9 g. (0.15 mole) of iodine was added over a 0.5 hour period. The resulting reaction mixture was held for 2 hours at 40° to 45° C. Analysis showed that the resulting iodophor product had 20.7% available iodine and 29.2% total iodine. This complexed compound was stable over 2 weeks at 50° C. and did not deposit iodine when diluted with water.

EXAMPLE 8

Preparation of

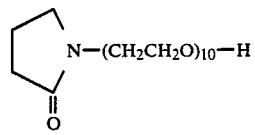

To 110.0 g. (1.29 moles) of pyrrolidone containing 0.5 g. of sodium hydroxide flakes, was gradually added 560 g. (12.9 moles) of ethylene oxide. After 5 hours, the product was cooled and analysis by NMR showed that 10.6 moles of ethylene oxide had reacted.

EXAMPLE 9

Preparation of

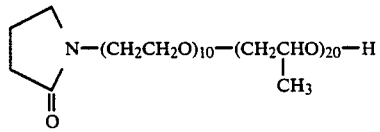

To 200 g. (0.38 mole) of 2-pyrrolidone-10-EO adduct obtained by Example 8 was added 440 g. (7.0 mole) of propylene oxide at a temperature of 160° C. under 30 psig pressure. After 5 hours the resulting product was neutralized with phosphoric acid and was found to have a cloud point of 39° C. (1% in water). NMR analysis indicated that 18 moles of propylene oxide had reacted.

The iodophor of the above product is prepared by adding 20.6 g. of sodium iodide in 18.6 g. of water to 168.5 g. (0.1 mole) of the pyrrolidone-EO-PO adduct at 40°-45° C. To this mixture, 56.5 g. (0.22 mole) of iodine is added and the resulting mixture stirred for 2 hours at 40°-45° C. Analysis showed that the complexed product contained 19.4% available iodine and 28.0% total iodine. This product was stable for 2 weeks at 50° C.

EXAMPLE 10

Preparation of

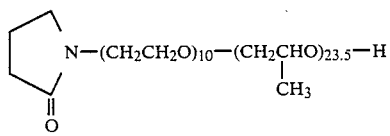

Example 9 is repeated except that 23.5 moles of propylene oxide is substituted therein. NMR analysis indicated that 23.5 moles of PO had reacted. The iodophor of this product is prepared by the procedure outlined in Example 9.

EXAMPLE 11

Preparation of

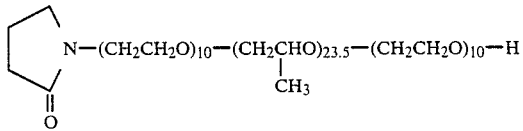

To the product of Example 10 is added 10 moles of ethylene oxide at a temperature of 160° C. under 30 psig. After 30 minutes the product is cooled and neutralized and analysis indicated the cloud point to be 40°-43° C. (1% in water).

The iodophor of the above product is prepared by adding to 189 g. (0.08 mole) of the above adduct obtained in Example 11, at a temperature of 40°-45° C., 29.0 g. of sodium iodide in 22.0 g. of water and 83.2 g. of iodine. The mixture is held for 2 hours at 40°-45° C., after which the product is cooled to room temperature. Analysis showed that the resulting iodophor product contained 23.12% available iodine and 32.9% total iodine.

EXAMPLE 12

Preparation of

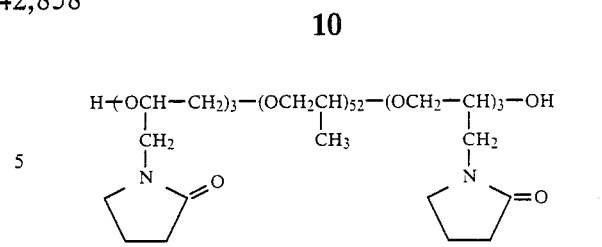

Into a one liter autoclave was charged 302.5 g. (0.1 mole) of propylene glycol (molecular wt. 3025) and 0.2 grams of potassium hydroxide. The mixture was heated to 110°-115° C. and held for 1 hour with a nitrogen sparge. Over a period of 30 minutes, 84.6 g. (0.6 mole) of 2,3-epoxypropyl-2-pyrrolidone was charged to the above solution and, after the addition was completed, the resulting mixture was held for 2 hours at 115° C. The product was then cooled and neutralized with 0.2 g. of glacial acetic acid. The product had a cloud point of 17.5°-18° C. (1% in water).

The iodophor of the above adduct was made according to the method described in Example 1 except that the adduct of Example 12 is substituted therein.

EXAMPLE 13

Preparation of

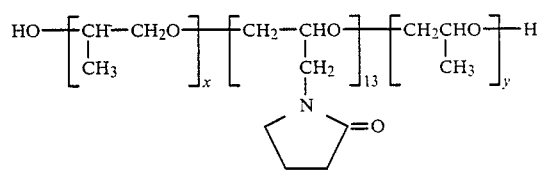

wherein the sum of x and y is 30.

N-Epoxypropyl pyrrolidone homopolymer having a number average molecular weight of 1900 is prepared by the method of F. P. sidelkovskaya (Vysokomol. Soedin Ser. B, 10(3), 187-189, 1968). To 1900 g or 1 mole of the homopolymer is added 0.1 wt. % of potassium hydroxide and 30 moles of propylene oxide at a temperature of 110°-125° C. under 50 to 75 psig. After all propylene oxide is reacted or taken up (about 7 hours) the resulting copolymer is cooled neutralized with phosphoric acid, and recovered by washing with water and drying.

The iodophor of the copolymer product is prepared by adding about 50 g. of iodine over a period of 30 minutes to a solution of 150 g. of the copolymer product in 13.3 g. of water containing 17.6 g. of sodium iodide at a temperature of 40°-45° C. The reaction mixture is then allowed to stand for 3 hours at 40°-45° C. after which it is cooled and recovered. The resulting iodine complex has at least 20% available iodine.

EXAMPLE 14

The extended time release and stability of the following iodophors were measured after 2 weeks at 50° C. The results of these tests are reported below.

Compound tested Cloud Point 1% in H$_2$O

| Compound tested | Cloud Point 1% in H$_2$O |
|---|---|
| A  N—(PO)$_{10}$—(EO)$_{10}$—H (pyrrolidone, C=O) |  |
| B  N—(PO)$_{20}$—(EO)$_{10}$—H (pyrrolidone, C=O) |  |
| C  N—(EO)$_{10}$—(PO)$_{20}$—H (pyrrolidone, C=O) |  |
| D  N—(EO)$_{10}$—(PO)$_{23.5}$—(EO)$_{10}$—H (pyrrolidone, C=O) |  |

|   |   | Initial % Available Iodine | % Total Iodine | Ratio I$^-$–I | Final* % Available Iodine |
|---|---|---|---|---|---|
| E | Iodine Complex of A | 20.60 | 28.7 | 0.30 | 19.55 |
| F | Iodine Complex of B | 20.70 | 29.2 | 0.30 | 19.90 |
| G | Iodine Complex of C | 19.45 | 28.0 | 0.30 | 19.45 |
| H | Iodine Complex of D | 23.12 | 32.96 | 0.35 | 21.93 |

*after 2 weeks at 50° C.

EXAMPLE 15

The low foaming or foam deterrent properties of the following iodophors were tested using the standard Waring blender test. A 180 ml sample of each of the following formulations was mixed at high speed for 3 minutes. The initial foam height immediately after mixing was measured, and the foam height was remeasured after 5 minutes. The results of these tests are as follows:

| Formulation | I | II | III | IV |
|---|---|---|---|---|
| Nonionic Surfactants |  |  |  |  |
| Igepal CO-660 (1) | 30.00 g |  |  |  |
| Compound A of Ex. 14 |  | 30.00 g |  |  |
| Compound B of Ex. 14 |  |  | 30.00 g |  |
| Compound D of Ex. 14 |  |  |  | 30.00 g |
| Iodophor |  |  |  |  |
| I-Complex of Igepal CO-660 | 46.00 g |  |  |  |
| I-Complex E in Ex. 14 |  | 46.00 g |  |  |
| I-Complex F in Ex. 14 |  |  | 46.00 g |  |
| I-Complex H in Ex. 14 |  |  |  | 46.00 g |
| 75% Phosphoric Acid | 83.75 g | 83.75 g | 83.75 g | 83.75 g |
| Propylene Glycol | 20.00 g | 20.00 g | 20.00 g | 20.00 g |
| Distilled Water | 70.25 g | 70.25 g | 70.25 g | 70.25 g |

(1) C$_9$H$_{19}$—C$_6$H$_4$—O—(CH$_2$CH$_2$O)$_{10}$CH$_2$CH$_2$OH

Foam Test

| Formulation | Initial Foam | Foam after 5 min. |
|---|---|---|
| I | 17.1 mm | 17.1 mm |
| II | 14.4 mm | 0.0 mm |
| III | 8.1 mm | 3.6 mm |
| IV | 9.0 mm | 5.4 mm |

Comparison of Formulations II, III and IV containing the alkyleneoxy pyrrolidonyl iodophors with formulation I containing closely related alkyleneoxy iodophors establish the present iodophors as low foaming agents.

All of the above iodophor products in the foregoing Examples possess excellent surfactant and disinfectant properties. It is to be understood that any of the other polymers set forth in the disclosure can be substituted in the Examples for the preparation of their corresponding iodophors having the desirable properties of this invention. Also bromine can be substituted in the examples to provide the corresponding bromophors.

What is claimed is:

1. The process of adding to a detergent solution an effective cleansing and disinfecting amount of the halogen complex selected from the group consisting of an iodine complex and a bromine complex of an alkyleneoxy lactam polymer containing between about 2 and about 40% halogen and said polymer contains (i) at least one pyrrolidonyl unit having the formula

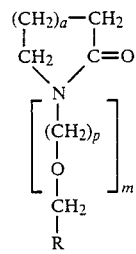

wherein a has a value of 1–3; p has a value of 1–2; m has a value of 0–1; R is a radical selected from the group of

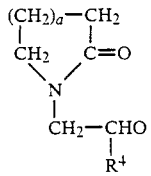

2. The process of claim 1 wherein the complex is an iodophor and between about 0.1 and about 15 weight % of the iodophor based on active ingredients is added to the detergent solution.

3. The process of claim 1 wherein said alkyleneoxy lactam polymer has the structure

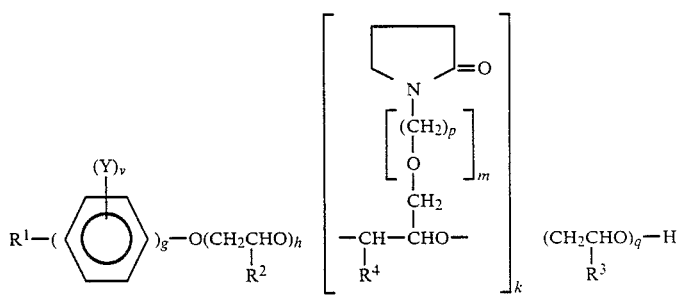

wherein at least one of $R^2$ and $R^3$ is methyl and the remaining $R^2$ and $R^3$ is methyl or hydrogen; h has a total value of 0–100; k has a total value of 2 to 200 and q has a total value of 0–100 and at least one of h and q is a positive integer; and $R^1$, $R^4$, Y, g, k, m, p and v are as defined in claim 1.

4. The process of claim 1 wherein said alkyleneoxy lactam polymer has the structure selected from the group of

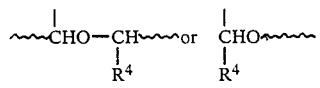

and wherein $R^4$ is hydrogen or methyl;
(ii) at least two propyleneoxy units
or
(iii) at least two propyleneoxy units and one or more ethyleneoxy units; and said polymer having terminal groups selected from the group consisting of hydroxy and the radical

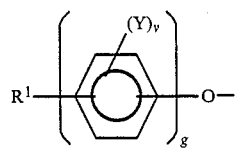

wherein $R^1$ is alkyl having from 6 to 20 carbon atoms; Y is alkyl having from 1 to 4 carbon atoms; v has a value of 0–2 and g has a value of 0–1; and, when m is O, the polymer contains only one of said lactam units,

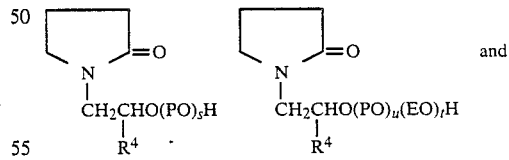

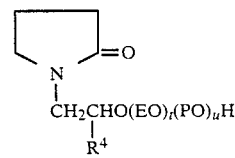

wherein $R^4$ is hydrogen or methyl; s has a value of 2 to 200; t has a total value of 2 to 50; u has a total value of 2 to 50; EO is ethyleneoxy and PO is propyleneoxy.

5. The process of claim 1 wherein said alkyleneoxy lactam polymer has the structure

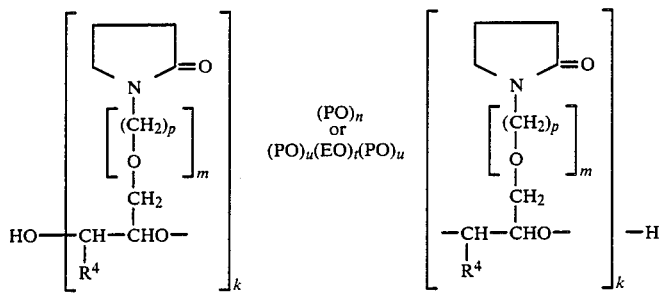

wherein n has a total value of 1–100; m has a value of 0 or 1; t has a total value of 2–50; u has a total value of 2–50; k has a total value of 2–200; EO is ethyleneoxy and PO is propyleneoxy.

6. The process of claim 1 wherein said alkyleneoxy lactam polymer has the structure

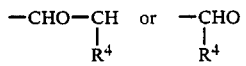

and wherein $R^4$ is hydrogen or methyl;

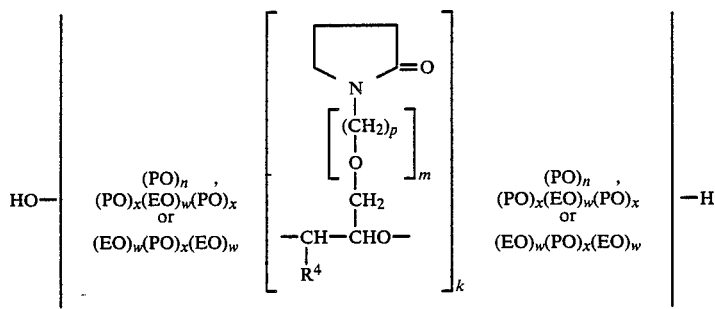

wherein k has a total value of 2–200; n has a total value of 1–100; m has a value of 0 or 1; w has a total value of 1–25; x has a total value of 1–25; EO is ethyleneoxy and PO is propyleneoxy.

7. The process for extending the gradual release of halogen which comprises adding to a topical medicinal solution an effective disinfecting amount of the halogen complex selected from the group of a iodine complex and a bromine complex of an alkyleneoxy lactam polymer containing between about 2 and about 40% halogen and said polymer contains (i) at least one pyrrolidonyl unit having the formula

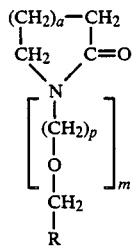

wherein a has a value of 1–3; p has a value of 1–2; m has a value of 0–1; R is a radical selected from the group of (ii) at least two propyleneoxy units or
(iii) at least two propyleneoxy units and one or more ethyleneoxy units; and said polymer having terminal groups selected from the group consisting of hydroxy and the radical

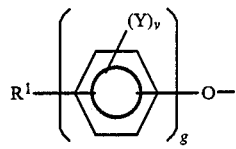

wherein $R^1$ is alkyl having from 6 to 20 carbon atoms; Y is alkyl having from 1 to 4 carbon atoms; v has a value of 0–2 and g has a value of 0–1; and, when m is O, the polymer contains only one of said lactam units,

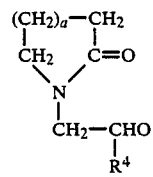

8. The process of claim 7 wherein said alkyleneoxy lactam polymer has the structure

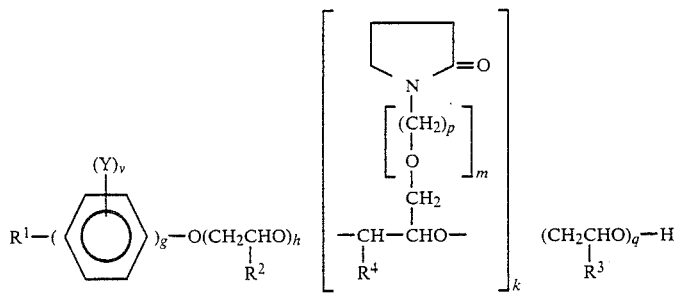

wherein at least one of $R^2$ and $R^3$ is methyl and the remaining $R^2$ and $R^3$ is methyl or hydrogen; h has a total value of 0–100; k has a total value of 2 to 200 and q has a total value of 0–100 and at least one of h and q is a positive integer; and $R^1$, $R^4$, Y, g, k, m, p and v are as defined in claim 1.

9. The process of claim 7 wherein said alkyleneoxy lactam polymer has the structure selected from the group of

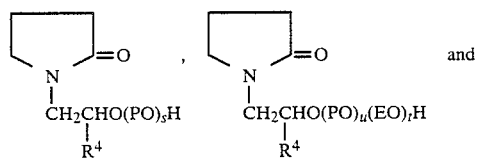 and

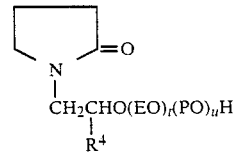

wherein $R^4$ is hydrogen or methyl; s has a value of 2 to 200; t has a total value of 2 to 50; u has a total value of 2 to 50; EO is ethyleneoxy and PO is propyleneoxy.

10. The process of claim 7 wherein said alkyleneoxy lactam polymer has the structure

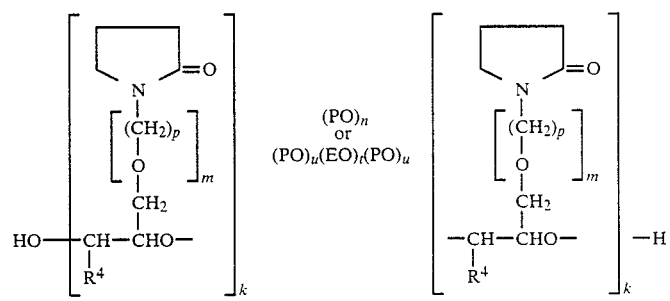

wherein n has a total value of 1–100; m has a value of 0 or 1; t has a total value of 2–50; u has a total value of 2–50; k has a total value of 2–200; EO is ethyleneoxy and PO is propyleneoxy.

11. The process of claim 7 wherein said alkyleneoxy lactam polymer has the structure

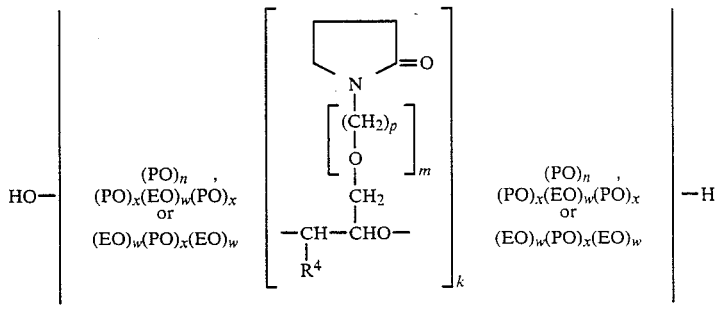

wherein k has a total value of 2–200; n has a total value of 1–100; m has a value of 0 or 1; w has a total value of 1–25; x has a total value of 1–25; EO is ethyleneoxy and PO is propyleneoxy.

12. The process of claim 7 wherein the complex is an iodophor and between about 0.1 and about 15 weight % of the iodophor based on active ingredients is added to the medicinal solution.

* * * * *